United States Patent
Lin et al.

(10) Patent No.: US 12,214,098 B2
(45) Date of Patent: Feb. 4, 2025

(54) CATALYST FOR GENERATING HYDROGEN PEROXIDE INDUCED BY TEMPERATURE DIFFERENCE AND METHOD FOR ENVIRONMENTAL DISINFECTION USING SAME

(71) Applicant: National Tsing Hua University, Hsinchu (TW)

(72) Inventors: Zong-Hong Lin, Hsinchu (TW); Yu-Jiung Lin, Hsinchu (TW); Imran Khan, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 712 days.

(21) Appl. No.: 17/522,875

(22) Filed: Nov. 9, 2021

(65) Prior Publication Data

US 2023/0048885 A1 Feb. 16, 2023

(30) Foreign Application Priority Data

Aug. 16, 2021 (TW) ................. 110130175

(51) Int. Cl.
*A61L 9/00* (2006.01)
*A61L 2/20* (2006.01)
(Continued)

(52) U.S. Cl.
CPC ............. *A61L 2/208* (2013.01); *A61L 2/26* (2013.01); *B01J 27/0576* (2013.01); *B01J 31/06* (2013.01);
(Continued)

(58) Field of Classification Search
CPC .... H01L 35/34; C08J 5/18; A61L 9/02; A61L 9/03
(Continued)

(56) References Cited

U.S. PATENT DOCUMENTS 10,651,360 B2 5/2020 Lee et al.

FOREIGN PATENT DOCUMENTS

CN 109922881 6/2019
CN 212039428 12/2020
(Continued)

OTHER PUBLICATIONS

European English Translation of the Description and the Claims Sections of TW 20146976 A.*
(Continued)

*Primary Examiner* — Monzer R Chorbaji
(74) *Attorney, Agent, or Firm* — JCIPRNET

(57) ABSTRACT

A catalyst adapted for generating hydrogen peroxide induced by a temperature difference and a method for environmental disinfection using the same are provided. The catalyst includes a thermoelectric material distributed on a substrate. The thermoelectric material induces a reaction between water vapor and oxygen contained in the air through a temperature difference to generate hydrogen peroxide, to serve a sterilization function through the hydrogen peroxide generated. The method for environmental disinfection using the catalyst includes the following. The catalyst is placed in an environment with a temperature difference. The catalyst is caused to induce a reaction between water vapor and oxygen contained in air through the temperature difference to generate hydrogen peroxide without applying power, and serve a sterilization function through the hydrogen peroxide generated.

12 Claims, 12 Drawing Sheets

(51) Int. Cl.
  *A61L 2/26* (2006.01)
  *B01J 27/057* (2006.01)
  *B01J 31/06* (2006.01)
  *B01J 35/50* (2024.01)
  *B01J 35/56* (2024.01)
  *H01B 1/02* (2006.01)

(52) U.S. Cl.
  CPC ............... *B01J 35/50* (2024.01); *B01J 35/56* (2024.01); *A61L 2202/11* (2013.01); *A61L 2202/25* (2013.01); *A61L 2202/26* (2013.01)

(58) Field of Classification Search
  USPC ................... 422/305–306; 252/514; 136/239
  See application file for complete search history.

(56) References Cited

FOREIGN PATENT DOCUMENTS

| | | | | |
|---|---|---|---|---|
| TW | 201406976 | | 2/2014 | |
| TW | 201406976 A | * | 2/2014 | ............. C22C 23/00 |
| TW | 201803154 | | 1/2018 | |

OTHER PUBLICATIONS

"Office Action of Taiwan Counterpart Application", issued on Feb. 10, 2022, p. 1-p. 4.
Yu-Jiung Lin et al., "Thermocatalytic hydrogen peroxide generation and environmental disinfection by Bi2Te3 nanoplates", Nature Communications, Jan. 2021, pp. 1-19.

* cited by examiner

CATALYST FOR GENERATING HYDROGEN PEROXIDE INDUCED BY TEMPERATURE DIFFERENCE AND METHOD FOR ENVIRONMENTAL DISINFECTION USING SAME

CROSS-REFERENCE TO RELATED APPLICATION

This application claims the priority benefit of Taiwanese application no. 110130175, filed on Aug. 16, 2021. The entirety of the above-mentioned patent application is hereby incorporated by reference herein and made a part of this specification.

BACKGROUND

Technical Field

The disclosure relates to a technology for environmental disinfection. Particularly, the disclosure relates to a catalyst for generating hydrogen peroxide induced by a temperature difference and a method for environmental disinfection using the same.

Description of Related Art

Due to the current severity of epidemic, the importance of a sterilization device is discovered. However, the current sterilization device and its technology typically require high costs in manufacturing and high power in operation.

Recently, two methods of generating ROS (reactive oxygen species) with renewable energy in place of the conventional chemical method have attracted wide attention from all fields. In one method, ROS is generated with a piezocatalyst through mechanical vibration; in the other, ROS is generated with a photocatalyst through light irradiation.

However, the absence of suitable mechanical forces in nature may prevent the realization of efficient piezocatalytic performance, leading the application of piezocatalysts into a bottleneck. On the other hand, where the photocatalyst is not under light irradiation or shaded, the photocatalytic reaction may be affected. Moreover, in practical applications, once in lack of sufficient light (e.g., in a rainy day or at night), round-the-clock photocatalytic performance may also be hindered by the unavailability of sunlight.

Therefore, it is currently needed to seek a high-efficiency catalyst adapted for an uninterrupted ROS generation at low costs.

SUMMARY

The disclosure provides a catalyst for generating hydrogen peroxide induced by a temperature difference, which catalyst can be widely used in the environment or daily life, and generates hydrogen peroxide ($H_2O_2$) induced by a temperature difference for disinfection and sterilization.

The disclosure also provides a method for environmental disinfection using the catalyst, in which disinfection and sterilization can be achieved by generating hydrogen peroxide without an external power source.

The catalyst for generating hydrogen peroxide induced by a temperature difference of the disclosure includes a thermoelectric material, which is distributed on a substrate and induces a reaction between water vapor and oxygen contained in air through a temperature difference to generate hydrogen peroxide ($H_2O_2$) to serve a sterilization function through the hydrogen peroxide generated.

In an embodiment of the disclosure, a form of the thermoelectric material includes a nanomaterial or a bulk.

In an embodiment of the disclosure, the nanomaterial includes a nanoparticle, a nanoplate, or a nanowire.

In an embodiment of the disclosure, the thermoelectric material is at least one material selected from a group consisting of a metal composite oxide, a polymer, a silicide, skutterudite, a Half-Heusler alloy, and a compound containing tellurium (Te).

In an embodiment of the disclosure, the thermoelectric material includes bismuth telluride ($Bi_2Te_3$), antimony telluride ($Sb_2Te_3$), or lead telluride (PbTe).

In an embodiment of the disclosure, the substrate includes a sheet substrate, a porous substrate, or a mesh substrate.

In an embodiment of the disclosure, a concentration of the hydrogen peroxide generated is modulated through a content of the thermoelectric material and/or a magnitude of the temperature difference.

In an embodiment of the disclosure, the thermoelectric material is formed on the substrate by coating, spraying, or soaking.

The method for environmental disinfection of the disclosure includes the following. The catalyst is placed in an environment with a temperature difference. The catalyst is caused to induce a reaction between water vapor and oxygen contained in air through the temperature difference to generate hydrogen peroxide without applying power, and serve a sterilization function through the hydrogen peroxide generated.

In another embodiment of the disclosure, the environment with the temperature difference includes an air outlet of an air conditioner, a heater, a fan, or a stove.

In another embodiment of the disclosure, the environment with the temperature difference includes a surface of a mask.

In another embodiment of the disclosure, the environment with the temperature difference includes an exterior wall or a window of a building.

Based on the foregoing, in the disclosure, a thermoelectric material is used as the catalyst, which may induce a reaction between water vapor and oxygen contained in the air through a temperature difference to generate hydrogen peroxide, and serve a sterilization function through the hydrogen peroxide generated. Moreover, power is not required to be applied with the use of the catalyst of the disclosure for environmental disinfection. As long as the catalyst is placed in an environment with a temperature difference, the catalyst may thus induce a reaction between water vapor and oxygen contained in the air to generate hydrogen peroxide.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
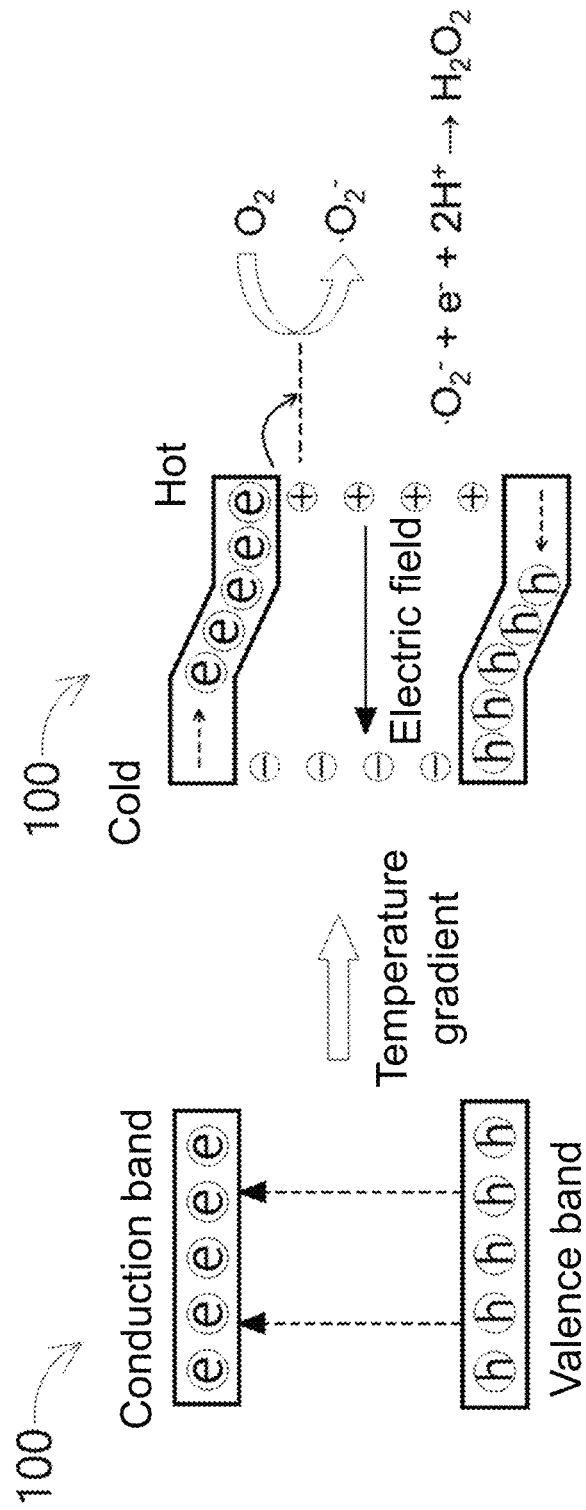
FIG. 1 is a schematic diagram of a thermocatalysis mechanism of a thermoelectric material according to an embodiment of the disclosure.

Exemplary embodiments of the disclosure with reference to the drawings will be comprehensively described below. However, the disclosure may still be embodied in many different forms and should not be interpreted as being limited to the embodiments described herein. For clarity in the drawings, sizes and shapes of structures and materials are possibly not drawn to actual scale.

First, in the disclosure uses thermoelectric material as the sterilization function of the catalyst's thermocatalysis mechanism as shown in FIG. 1.

With reference to FIG. 1 on the left, generally, the conduction band potential of a thermoelectric material 100 is more negative than the redox potential of $O_2/\cdot O_2^-$. Therefore, because of the relatively large potential difference present between the conduction band of thermoelectric material 100 and the redox potential of $O_2/\cdot O_2^-$, free charges present on the surface of the thermoelectric material 100 quickly exhaust before reacting with the bacteria, and no significant catalytic activity is present.

However, with the generation of a temperature difference, with reference to of FIG. 1 on the right, the band energy decreases at the positive potential side and increases at the negative potential side, such that the conduction band and the valence band of the thermoelectric material 100 tilt, negative charges rush from the code end to the hot end of the thermoelectric material 100 and produce a potential difference between the hot end and the cold end, and at the same time, the conduction band of the thermoelectric material 100 is also close to the redox potential of $O_2/\cdot O_2^-$. Consequently, electrons from the conduction band migrate to the surface of the thermoelectric material 100, and generate hydrogen peroxide ($H_2O_2$) via reaction formula (1) below.

$$\cdot O_2^- + e^- + 2H^+ \rightarrow H_2O_2 \qquad \text{formula (1)}$$

In the disclosure, the form of the thermoelectric material 100 may be a bulk or a nanomaterial. The term "bulk" herein represents a material with a micron-scale size, such as 0.5 cm to microns. The term "nanomaterial" herein represents a material with a nano-level size, and the nanomaterial includes a nanoparticle, a nanoplate, or a nanowire. For the thermoelectric material 100, common thermoelectric materials or materials prepared in a laboratory, at least one material selected from a group consisting of a metal composite oxide, a polymer, a silicide, skutterudite, a Half-Heusler alloy, and a compound containing tellurium (Te), for example, may be used. In some embodiments, the thermoelectric material 100 may include but is not limited to bismuth telluride ($Bi_2Te_3$), antimony telluride ($Sb_2Te_3$), or lead telluride (PbTe).

Figure 2A:
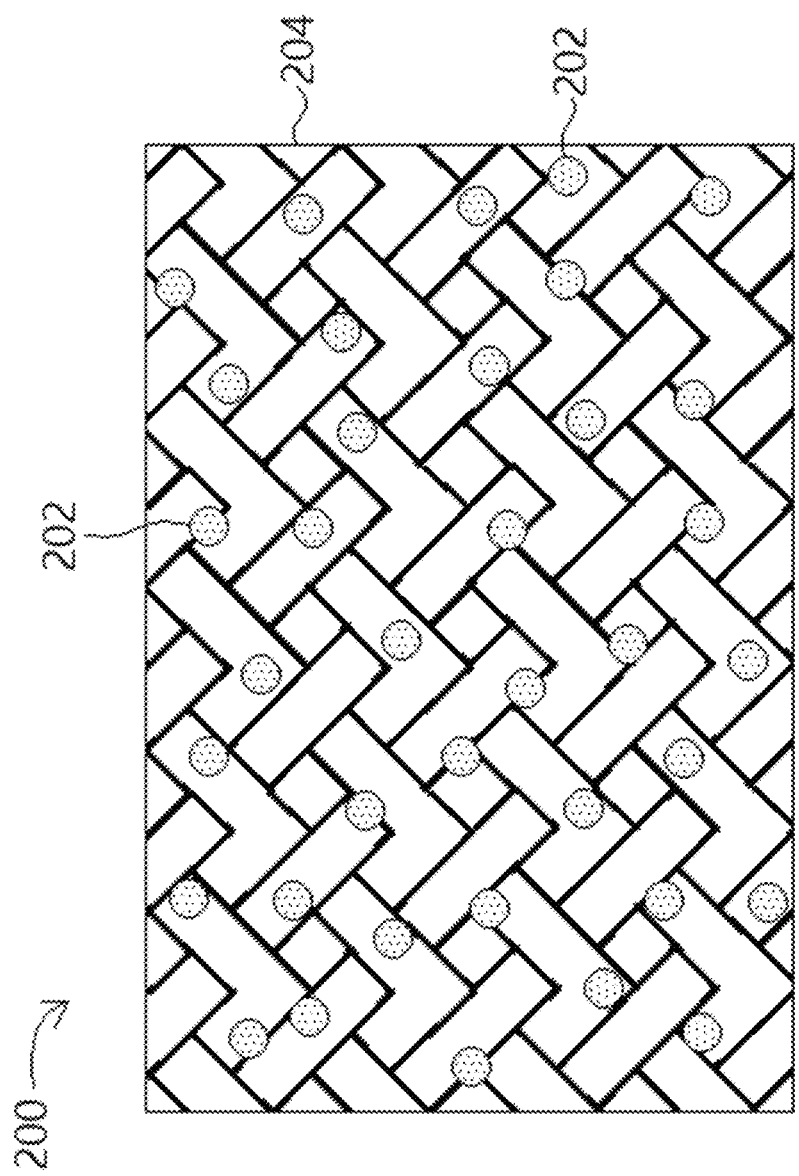
FIG. 2A is a schematic diagram of a catalyst for generating hydrogen peroxide induced by a temperature difference according to an embodiment of the disclosure.

FIG. 2A is a schematic diagram of a catalyst for generating hydrogen peroxide induced by a temperature difference of an embodiment according to the disclosure.

With reference to FIG. 2A, a catalyst 200 of this embodiment includes a thermoelectric material 202, which is distributed on a substrate 204. The thermoelectric material 202 may be formed on the substrate 204 by coating, spraying, or soaking. For the form of the thermoelectric material 202, reference may be made to the description of the thermoelectric material 100, which will not be repeated. The substrate 204 may include a sheet substrate, a porous substrate, or a mesh substrate. For example, the substrate 204 in FIG. 2A is a mesh substrate similar to a woven cloth, and the thermoelectric material 202 is a nanomaterial. However, the disclosure is not limited thereto. Depending on the environmental temperature, the type of each of the substrate 204 and the thermoelectric material 202 may be selected as appropriate to serve as a sterilization device.

Figure 2B:
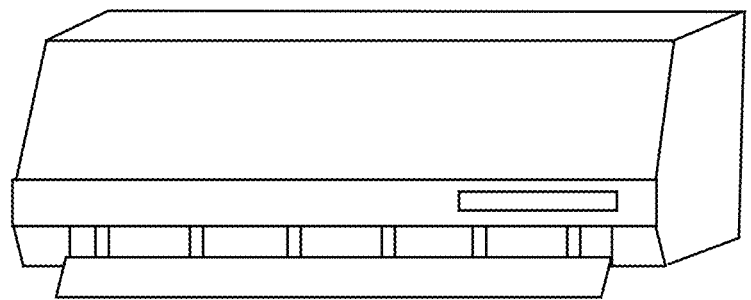
FIG. 2B is a schematic diagram of an air conditioner applying the catalyst of the disclosure.

For example, due to factors such as global warming, seasons with a relatively high temperature are present in whichever of the tropical, subtropical, or temperate zones. Accordingly, in the need of an air conditioner or a fan for cooling down, the thermoelectric material 202 may be formed on the surface of the substrate 204 such as a filter or woven cloth, and then mounted at the air outlet of the air conditioner as shown in FIG. 2B, to induce a reaction between water vapor and oxygen contained in the air by the environmental temperature difference to generate hydrogen peroxide. On the other hand, sub-zero temperatures often occur in the temperate or frigid zone, so a heater or stove is needed for increasing the temperature. Therefore, the thermoelectric material 202 may also be formed on the surface of the substrate 204, and then mounted at the air outlet of the air conditioner as shown in FIG. 2B, to induce generation of hydrogen peroxide by the environmental temperature difference. In this embodiment, the thermoelectric material 202 may be selected as appropriate depending on the temperature difference and the environmental temperature.

Figure 2C:
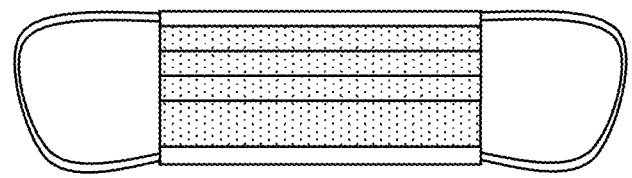
FIG. 2C is a schematic diagram of a mask applying the catalyst of the disclosure.

In addition, if the catalyst 200 is applied to an epidemic prevention product such as a mask as shown in FIG. 2C, generation of hydrogen peroxide for disinfection and sterilization may similarly be catalyzed by the temperature difference. Moreover, according to the content of the thermoelectric material 202 and/or the magnitude of the temperature difference, the concentration of the generated $H_2O_2$ may be modulated. Specifically, as the thermoelectric material 202 increases in content, the $H_2O_2$ increases in concentration; and as the temperature difference increases, the $H_2O_2$ also increases in concentration. Therefore, depending on the application area of the catalyst 200, the temperature difference may be first determined, and the content of the thermoelectric material 202 may then be changed to strike a balance between the requirements of sterilization function and prevention from a hazard to the human body.

The method for environmental disinfection of the disclosure include the following. The catalyst 200 of FIG. 2A is placed in an environment with a temperature difference. The catalyst is caused to induce a reaction between water vapor and oxygen contained in air through the temperature difference to generate hydrogen peroxide ($H_2O_2$) without applying power, and serve a sterilization function through the hydrogen peroxide generated.

In an embodiment, the environment with the temperature difference includes an air outlet of an air conditioner, a heater, a fan, or a stove.

In another embodiment, the environment with the temperature difference includes a surface of a mask.

In still another embodiment, the environment with the temperature difference includes an exterior wall or a window of a building.

Some experiments will be provided below to verify the effects of the disclosure, but the disclosure is not limited to the following content.

<Experimental Example 1> Analysis on Thermoelectric Material (Bulk)

The following thermocatalysis test was carried out using thermoelectric materials $Bi_2Te_3$, $Sb_2Te_3$, and PbTe (each purchased from Alfa Aeser) and a photocatalyst $TiO_2$, each in a bulk form.
1. Thermocatalysis Test The generation of superoxide radicals during the thermocatalysis reaction was estimated quantitatively by using XTT (2, 3-bis (2-methoxy-4-nitro-5-sulfophehyl)-2H-tetrazolium-5-carboxanilide) assay to obtain the generation efficiency.

Generally, an aqueous dispersion of the bulk was mixed with XTT (50 μM), and then the mixed solution was subjected to different temperature differences in a water bath. After the reaction, the bulk was separated by centrifugation, and the absorbance spectrum of the supernatant was detected at 470 nm. The estimated data is shown in FIG. 3A.

Figure 3A:
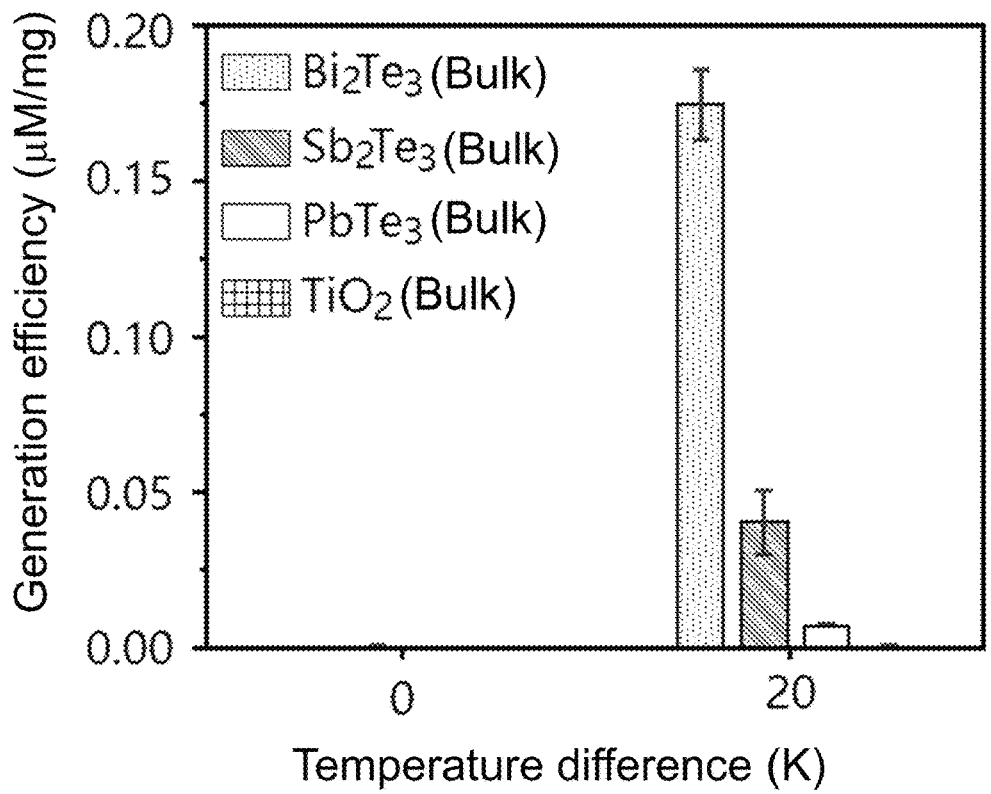
FIG. 3A is a bar graph of generation efficiency by different thermoelectric materials and a photocatalyst $TiO_2$ with or without a temperature difference in Experimental Example 1.

FIG. 3A is a bar graph of generation efficiency by different thermoelectric materials and the photocatalyst $TiO_2$ at a temperature difference of 0 and at a temperature difference of 20K. From FIG. 3A, it can be found that the thermoelectric material bulks each have capability of generating hydrogen peroxide through thermocatalysis, while $TiO_2$ hardly generates hydrogen peroxide under a temperature difference.

Next, the bulk $Bi_2Te_3$ with a higher generation efficiency in FIG. 3A was adopted for the following analysis.

First, based on the thermocatalysis test, the aqueous dispersion of the bulk $Bi_2Te_3$ was mixed with XTT (50 μM), and then the mixed solution was subjected to different temperature differences in a water bath. After the reaction, the bulk was separated by centrifugation, and the absorbance spectrum of the supernatant was detected at 470 nm. The estimated data is shown in FIG. 3B.

Figure 3B:
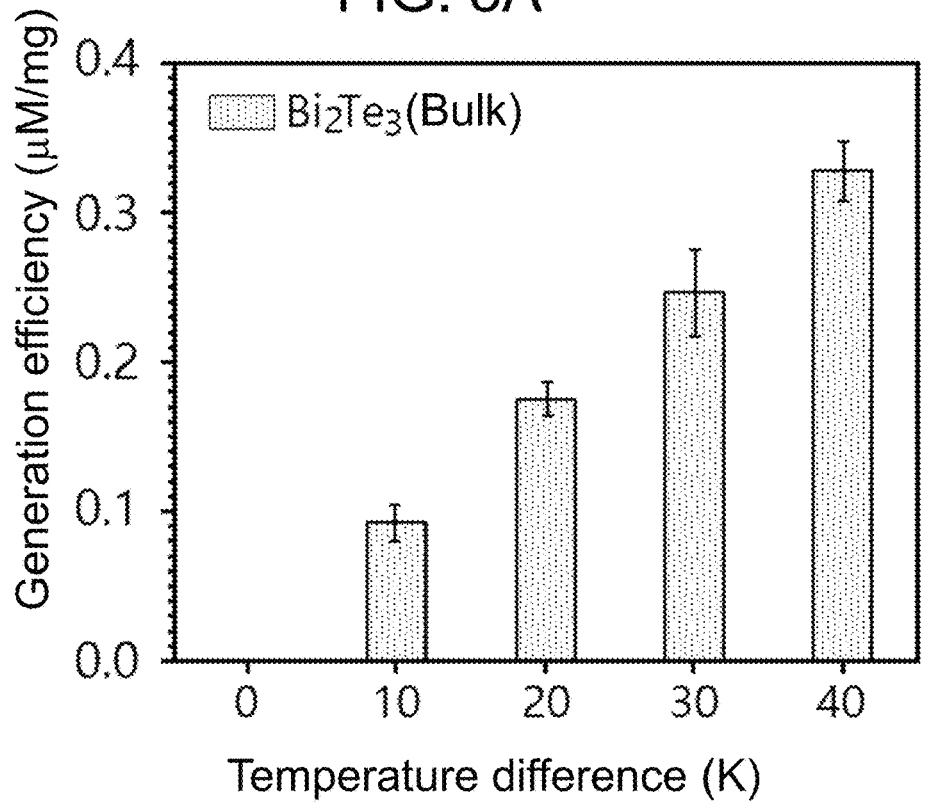
FIG. 3B is a bar graph of generation efficiency by a bulk $Bi_2Te_3$ of Experimental Example 1 under different temperature differences.

FIG. 3B is a bar graph of generation efficiency by the bulk $Bi_2Te_3$ (50 mg) under different temperature differences, which shows that a greater temperature difference indicates a higher generation efficiency. For example, the $H_2O_2$ generation efficiency at a temperature difference of 40K reached about 0.34 μM/mg.

Then, to verify the antibacterial effect of the generated $H_2O_2$, the following experiment was performed.
2. Disinfection (Antibacterial) Experiment First, E. coli K12 cells were grown in a lysogeny broth (LB) medium for 16 h at 37° C. Then, the E. coli K12 cells were diluted to an optical density of 0.06 at 670 nm (OD670=0.06). Further, the bacterial cell suspension was diluted 10 times with 0.85% sodium chloride, which was equal to $2\times10^7$ CFU per 1 mL for antibacterial investigation.

Next, the bulk $Bi_2Te_3$ (50 mg) was added into 1 mL of the bacterial solution ($2\times10^6$ CFU per 1 mL) and was subjected to 3 thermal cycles, respectively denoted as C1, C2, and C3.

In each thermal cycle, the material was first allowed to react at a specific temperature (15° C./35° C./45° C.) for 5 minutes, and then was returned to room temperature (25° C.) for 5 minutes. In addition, one group with no temperature difference (under room temperature) served as a control group.

Then, aliquots of 100 μL of the bacterial solution were collected and plated on an aseptic plate. The bacterial colonies were counted from the plate after 24 hours of incubation at 37° C. The survival rates were determined by using the formula $C/C_0\times100\%$, where $C_0$ is the concentration of the bacteria solution before thermal treatment, and C is the remaining concentration of the bacteria after the thermal treatment. The results are shown in FIG. 3C.

Figure 3C:
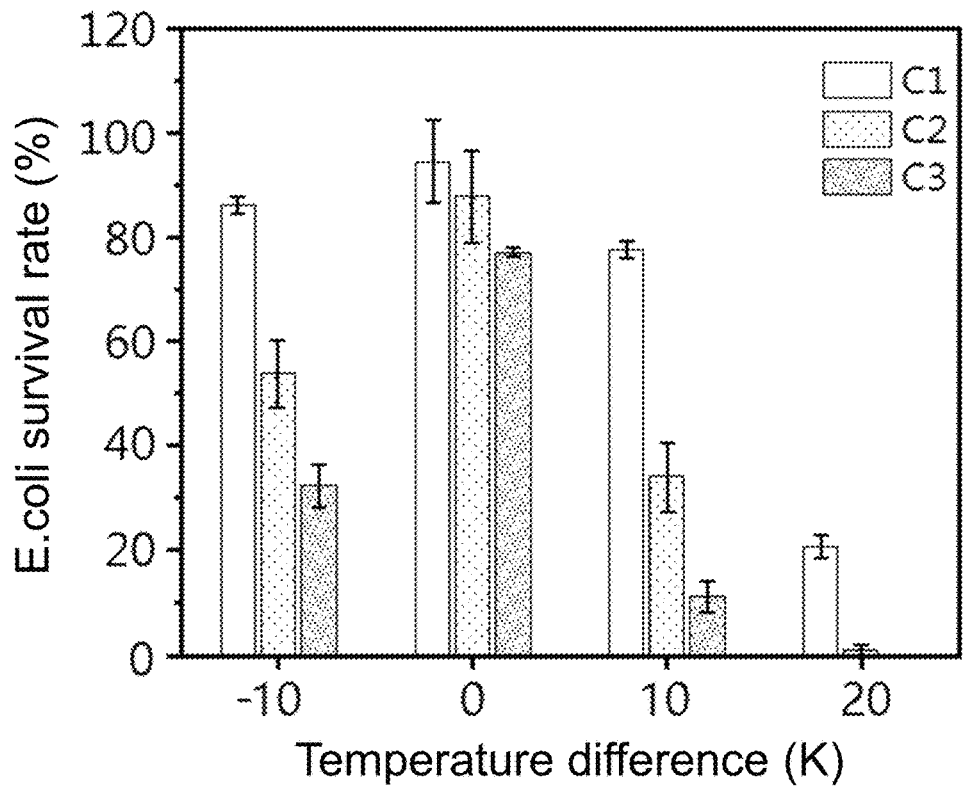
FIG. 3C is a bar graph of disinfection performance of the bulk $Bi_2Te_3$ of Experimental Example 1 under different temperature differences.

FIG. 3C is a bar graph of disinfection performance of the bulk $Bi_2Te_3$ (50 mg) under different temperature differences. From FIG. 3C, it can be found that as the number of thermal cycles increases from 1 (C1) to 3 (C3), the disinfection performance of the bulk $Bi_2Te_3$ increases gradually. This result also indicates that the disinfection performance has a positive correlation with the amount of hydrogen peroxide generated. In other words, higher hydrogen peroxide production caused by a greater temperature difference results in a better thermocatalytic effect, and in turn a greater disinfection performance.

To verify that the thermoelectric material as a catalyst does not participate in the reaction, the following $H_2O_2$ concentration detection was first performed, and then the weight of the bulk $Bi_2Te_3$ was measured to observe the change in weight of the bulk $Bi_2Te_3$ before and after the reaction.
3. $H_2O_2$ Concentration Detection An Amplex Red reagent with an HRP enzyme was used for $H_2O_2$ detection. In general, Amplex Red reacts with $H_2O_2$ to produce a red-fluorescent oxidation product, i.e., resorufin.

First, two different stock solutions were prepared. One was 0.4 mg Amplex Red powder dissolved in 3.1 mL dimethyl sulfoxide (DMSO), and the other was 0.5 mg of HRP dissolved in phosphate-buffered saline (PBS, pH 5.8). Then, the bulk was first added into 1 mL of a sodium chloride (0.85% NaCl) solution, and then the solution was placed in a water bath for 15 minutes at a temperature difference of 20K.

After the temperature treatment, the solution was filtered by a 0.2 μm PVDF membrane filter, and 270 μL of the filtrate solution was added into a mixture of 30 μL of the Amplex Red solution and 3 μL of the HRP solution. A photoluminescence spectrophotometer (HITACHI F-7000) was used to detect the generated fluorescent product. That is, the sample was excited at 530 nm, and the emission spectrum was scanned from 560 to 750 nm. The $H_2O_2$ concentrations under different thermal cycles obtained are shown in FIG. 3D.

Figure 3D:
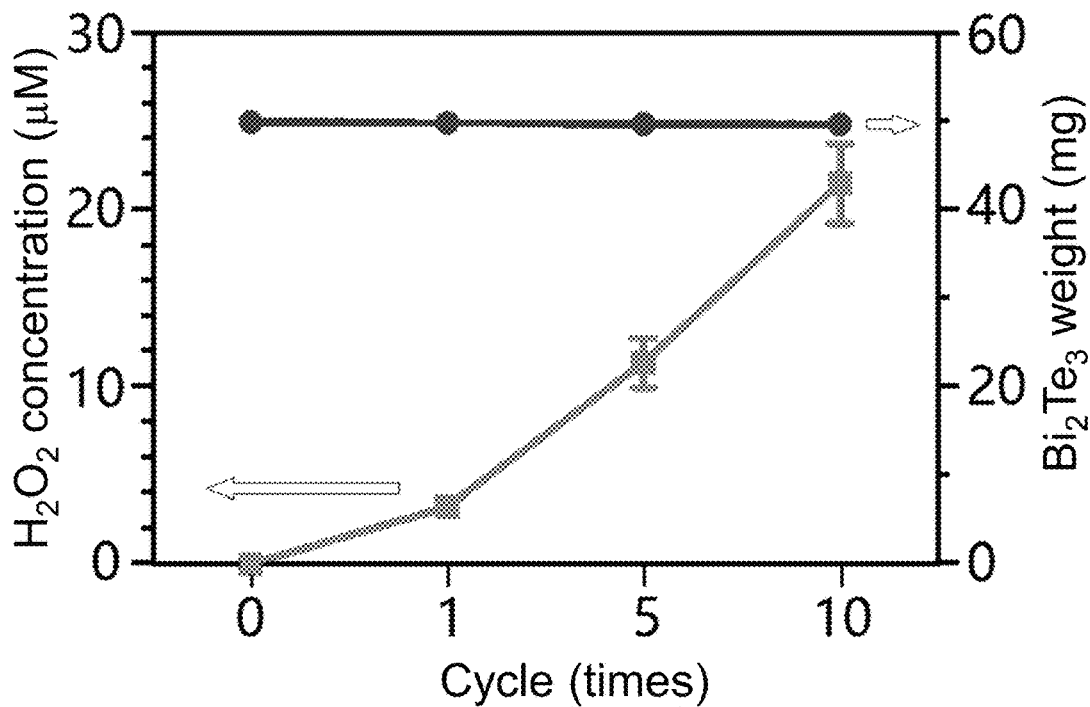
FIG. 3D is a line graph of changes of $H_2O_2$ concentration and weight of $Bi_2Te_3$ of the bulk $Bi_2Te_3$ of Experimental Example 1 under different thermal cycles.

FIG. 3D also shows the measured weight of the bulk $Bi_2Te_3$ after different thermal cycles. Accordingly, it can be found from FIG. 3D that, for the bulk $Bi_2Te_3$ of Experimental Example 1, as the number of thermal cycles increases from 1 to 10, the $H_2O_2$ concentration increases gradually, but the weight of the bulk $Bi_2Te_3$ is substantially maintained at 50 mg. Therefore, the thermoelectric material serves as a catalyst during the process of $H_2O_2$ generation.

Figure 3E:
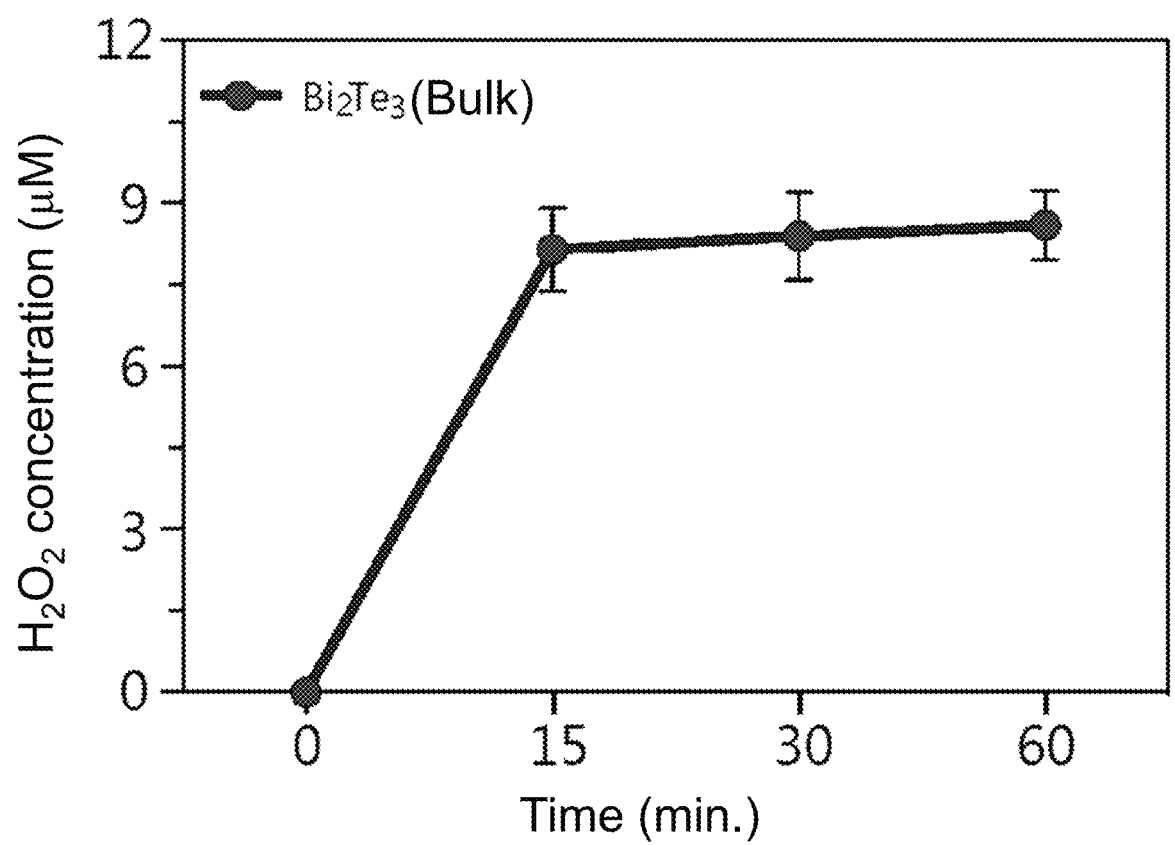
FIG. 3E is a line graph of a change of $H_2O_2$ concentration of the bulk $Bi_2Te_3$ of Experimental Example 1 under a change of temperature.

In addition, during the detection process of the adopted $H_2O_2$ concentration detection, the temperature difference was only present in the first 15 minutes, while the environmental temperature was subsequently kept constant, and a line graph of a change of the $H_2O_2$ concentration of the bulk $Bi_2Te_3$ under a temperature change is obtained in FIG. 3E. From FIG. 3E, it can be observed that once no temperature difference is present, the $H_2O_2$ concentration is substantially unchanged, which indicates that barely any more $H_2O_2$ is produced since the $15^{th}$ minute. Therefore, the temperature difference obviously affects $H_2O_2$ generation through thermocatalysis.

<Preparation Example 1> Preparation of a Nanomaterial $Bi_2Te_3$

First, a stock solution was prepared by dissolving 0.8 g of sodium hydroxide in 10 mL of ethylene glycol at 45° C. in a water bath. Then, 0.1 g of bismuth nitrate pentahydrate, 0.067 g of sodium telluride, and 0.235 g of polyvinylpyrrolidone (PVP) were loaded into a 25 mL three-necked flask, into which 10 mL of the stock solution was added. The mixture was stirred for 10 minutes at room temperature.

After that, the three-neck flask was placed in a water bath at 45° C. for 20 minutes. Until the precursors were dissolved in the solution, the three-neck flask was kept in an oil bath and stirred for 3 hours at 190° C. After the reaction, 30 mL of isopropyl alcohol and 10 ml of acetone were added into the solution, and the mixture was centrifuged at 6700×g for 10 minutes. The supernatant was discarded, and the process was repeated 3 times. Finally, the filtered $Bi_2Te_3$ nanoplate was redispersed in 30 mL of isopropyl alcohol and was used for further experiments.

<Experimental Example 2> Analysis of Thermoelectric Material (Nanomaterial)

Figure 4A:
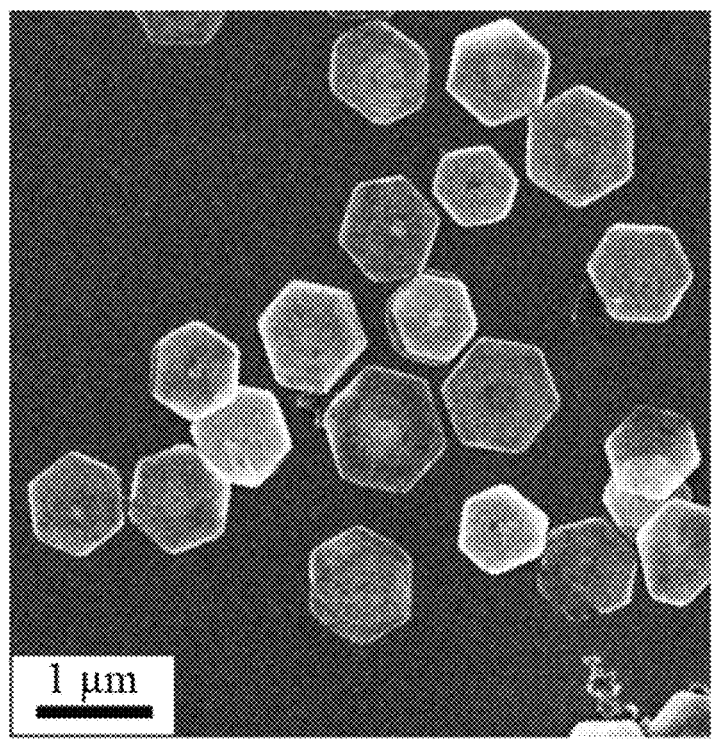
FIG. 4A is an SEM image of a nanomaterial $Bi_2Te_3$ of Experimental Example 2.

First, the $Bi_2Te_3$ nanoplate obtained in Preparation Example 1 was observed with a field emission scanning electron microscope (FESEM), which is shown in FIG. 4A. From FIG. 4A, it can be observed that $Bi_2Te_3$ is a uniform hexagonal nanoplate-like nanomaterial.

Figure 4B:
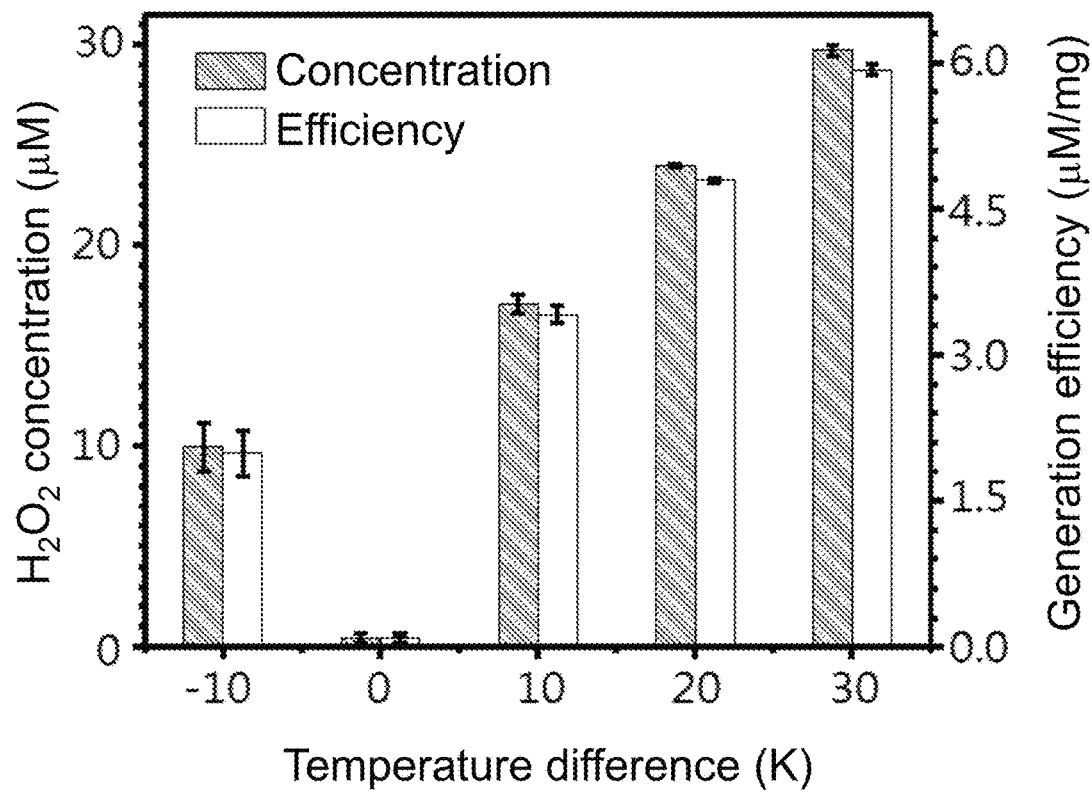
FIG. 4B is a bar graph of $H_2O_2$ concentration of and generation efficiency by the nanomaterial $Bi_2Te_3$ of Experimental Example 2 under different temperature differences.

Then, the thermocatalysis test and $H_2O_2$ concentration detection of Experimental Example 1 were used, in which the bulk was changed into the $Bi_2Te_3$ nanoplate (5 mg) obtained in Preparation Example 1, and the $H_2O_2$ concentration and production efficiency of the nanomaterial $Bi_2Te_3$ under different temperature differences can be obtained, which are shown in FIG. 4B. From FIG. 4B, it can be found that a greater temperature difference indicates both a greater $H_2O_2$ concentration and a higher generation efficiency. Moreover, $H_2O_2$ can be generated regardless of whether the temperature difference is positive or negative. For example, at a temperature difference of 30K, only 5 mg of a $Bi_2Te_3$ nanoplate can reach a $H_2O_2$ concentration of about 30 μM. Therefore, in terms of generation efficiency, a $Bi_2Te_3$ nanoplate exhibits a more than 20 times higher generation efficiency than a bulk $Bi_2Te_3$.

Figure 4C:
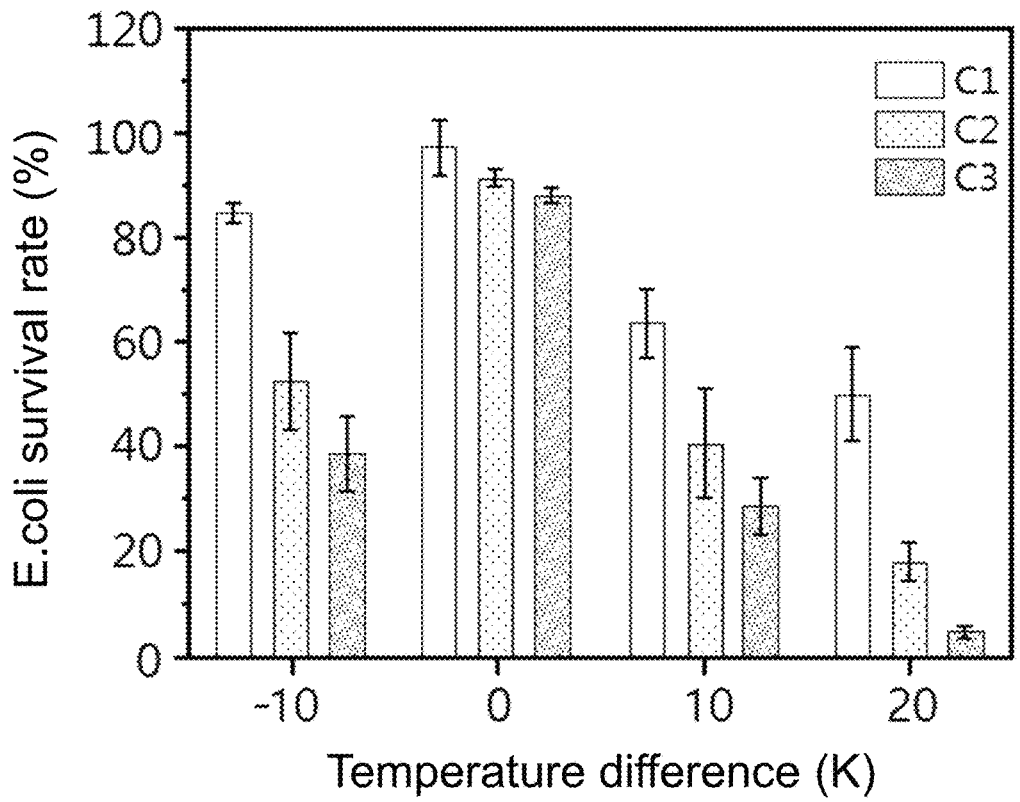
FIG. 4C is a bar graph of disinfection performance of the nanomaterial $Bi_2Te_3$ of Experimental Example 2 after three thermal cycles under different temperature differences.

In addition, the disinfection (antibacterial) experiment of Experimental Example 1 was used, in which the bulk was changed into the $Bi_2Te_3$ nanoplate (5 mg) obtained in Preparation Example 1, and the disinfection performance of the nanomaterial $Bi_2Te_3$ after three thermal cycles under different temperature differences can be obtained, which is shown in FIG. 4C. From FIG. 4C, it can be found that as the number of thermal cycles increases, the disinfection performance of the nanomaterial $Bi_2Te_3$ increases gradually.

Experimental Example 3

First, a surface potential analysis of the $Bi_2Te_3$ nanoplate was carried out by Kelvin probe force microscopy (KPFM), and it was observed that the surface of the $Bi_2Te_3$ nanoplate did not show any surface potential in the thermal equilibrium. However, a response voltage of ~280 mV was observed at a temperature of 60° C.

Figure 5:
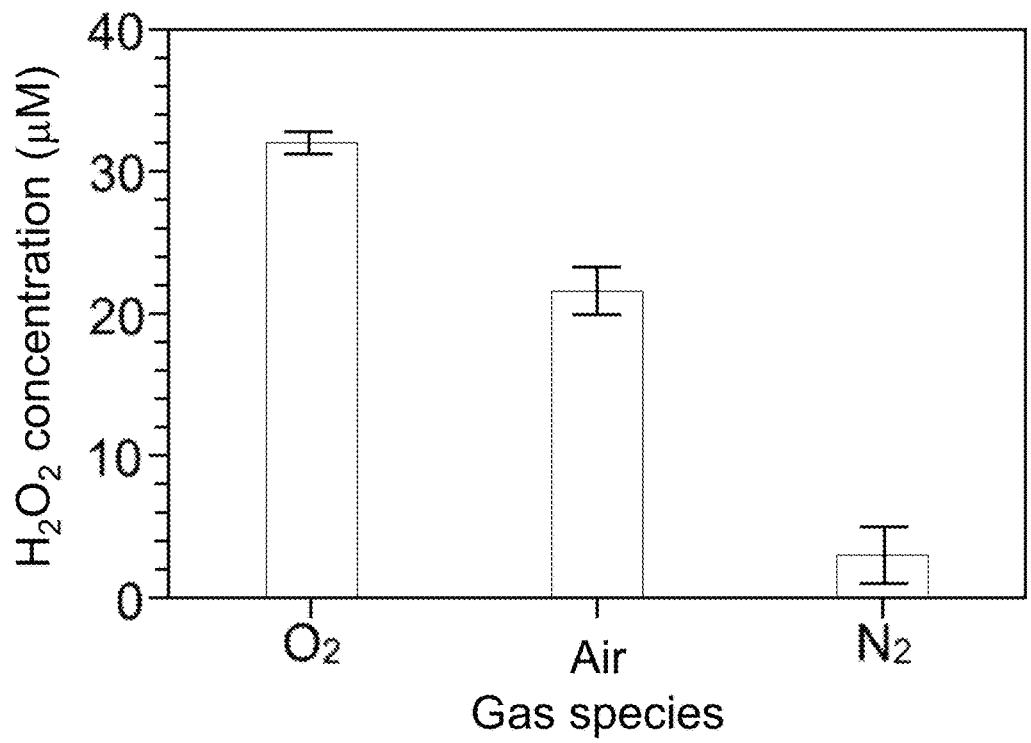
FIG. 5 is a bar graph of $H_2O_2$ concentration of a nanomaterial $Bi_2Te_3$ of Experimental Example 3 in different gas environments.

In addition, the $H_2O_2$ concentration (at a temperature difference of 20K) was tested for $Bi_2Te_3$ under different environmental conditions (including $O_2$, $N_2$, and air), and the results are shown in FIG. 5. From FIG. 5, it can be found that an $N_2$-filled environment led to the lowest amount of $H_2O_2$ generated, and an $O_2$-filled environment led to the greatest amount of $H_2O_2$ generated, verifying that superoxide radicals from $O_2$ decomposition are a key factor in $H_2O_2$ generation.

<Preparation Example 2> Preparation of $Bi_2Te_3$@CFF

To clean the surface of a carbon fiber fabric (CFF), the carbon fiber fabric was soaked in acetone, isopropanol, and deionized water for 5 minutes, respectively. Then, the carbon fiber fabric was cut into a size of 1×1 cm and dipped in 100 μL of a $Bi_2Te_3$ nanoplate (1 mM; $Bi_2Te_3$ nanoplate of Preparation Example 1) solution. Finally, the prepared carbon fiber was dried in a hot air oven to completely remove the water.

Experimental Example 4

To prove that $Bi_2Te_3$@CFF serves as a catalyst with an antibacterial performance, the following test was carried out.

Figure 6A:
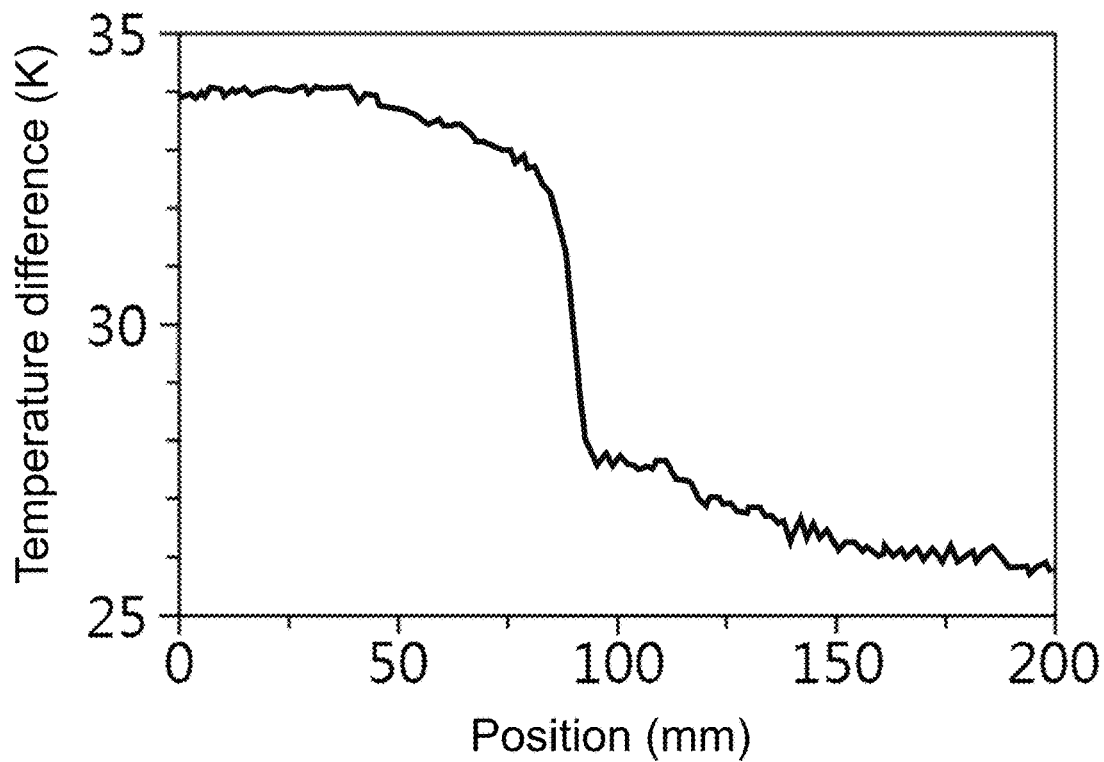
FIG. 6A is a temperature profile of a catalyst of Experimental Example 4 during exposure to cold air.

First, a bacterial solution (2×10⁶ CFU/mL) was prepared by the method in the disinfection (antibacterial) experiment of Experimental Example 1. Then, 1 mL of the bacterial solution was added into each of 1×1 cm $Bi_2Te_3$@CFF and 1×1 cm commercially available CFF, and further treated for a total time of 20 minutes under the temperature difference created by a hairdryer and a cooling fan. Control experiments were also performed under the same conditions without the temperature difference. FIG. 6A is a temperature profile of the tested samples during exposure to cold air, and FIG. 6B is a temperature profile of the tested samples during exposure to hot air.

The treated $Bi_2Te_3$@CFF and CFF were immersed into 1 mL of 0.85% sodium chloride solution. Then, aliquots of 100 μL of the bacterial solution were collected and plated on an aseptic plate. The bacterial colonies were counted from the plate after 24 hours of incubation at 37° C. The survival rates were determined by using the formula $C/C_0 \times 100\%$, where $C_0$ is the concentration of the bacteria solution before thermal treatment, and C is the remaining concentration of the bacteria after the thermal treatment. The results are shown in FIG. 6C and FIG. 6D.

Figure 6B:
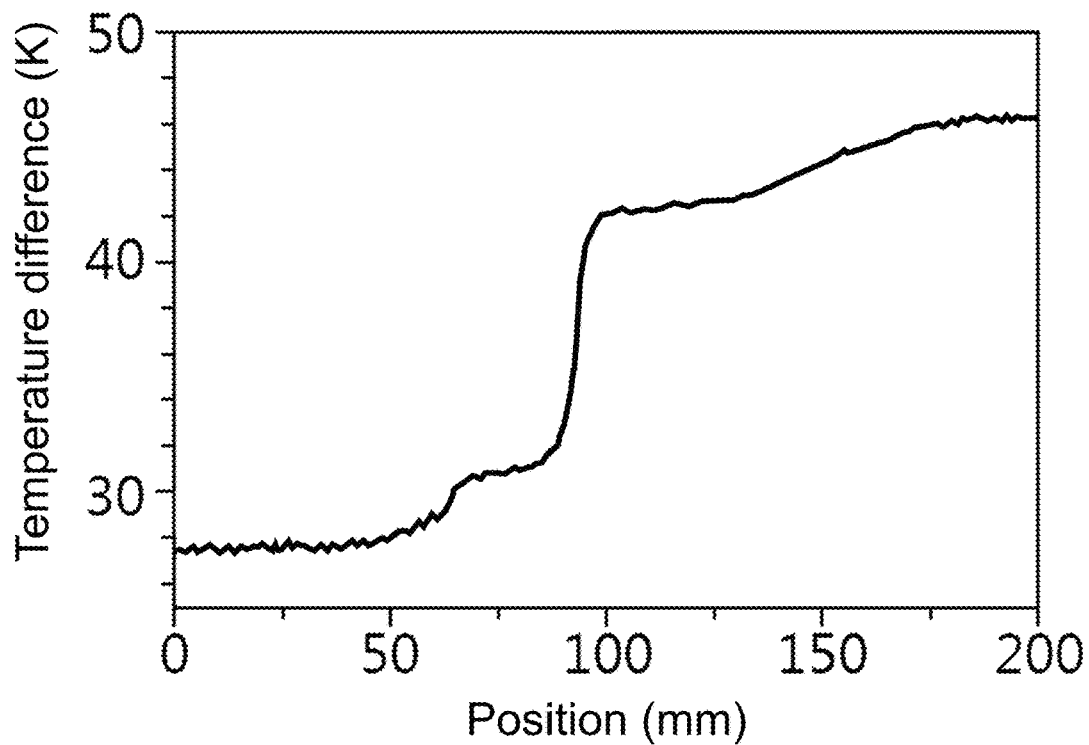
FIG. 6B is a temperature profile of the catalyst of Experimental Example 4 during exposure to hot air.
Figure 6C:
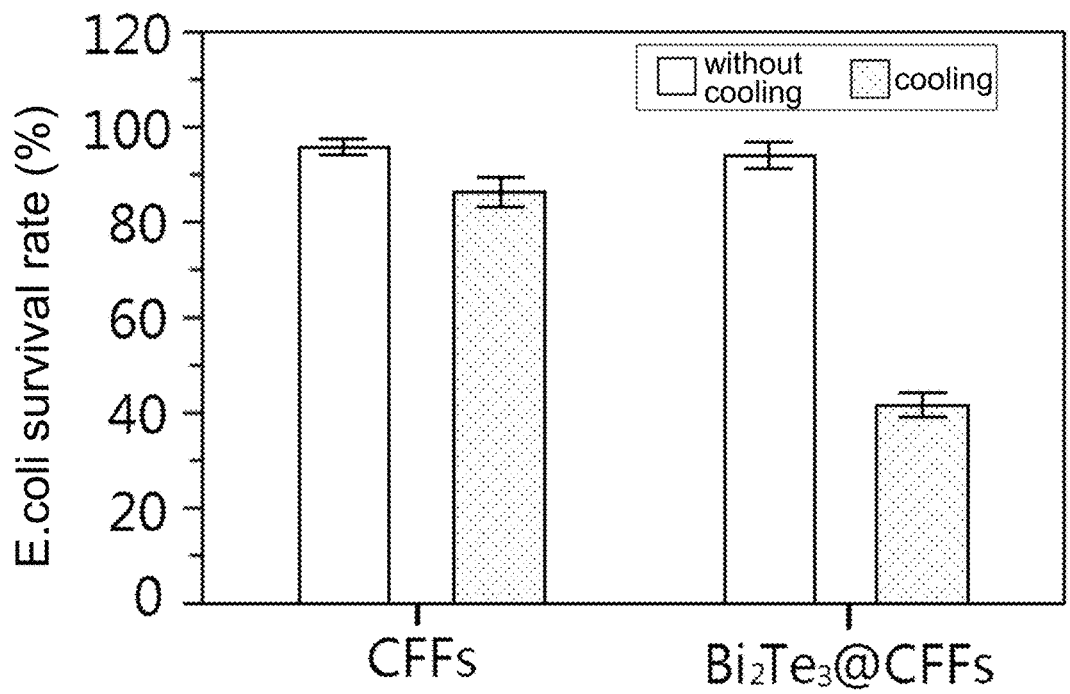
FIG. 6C is a bar graph of disinfection performance of the catalyst and a substrate of Experimental Example 4 under the temperature difference of FIG. 6A.
Figure 6D:
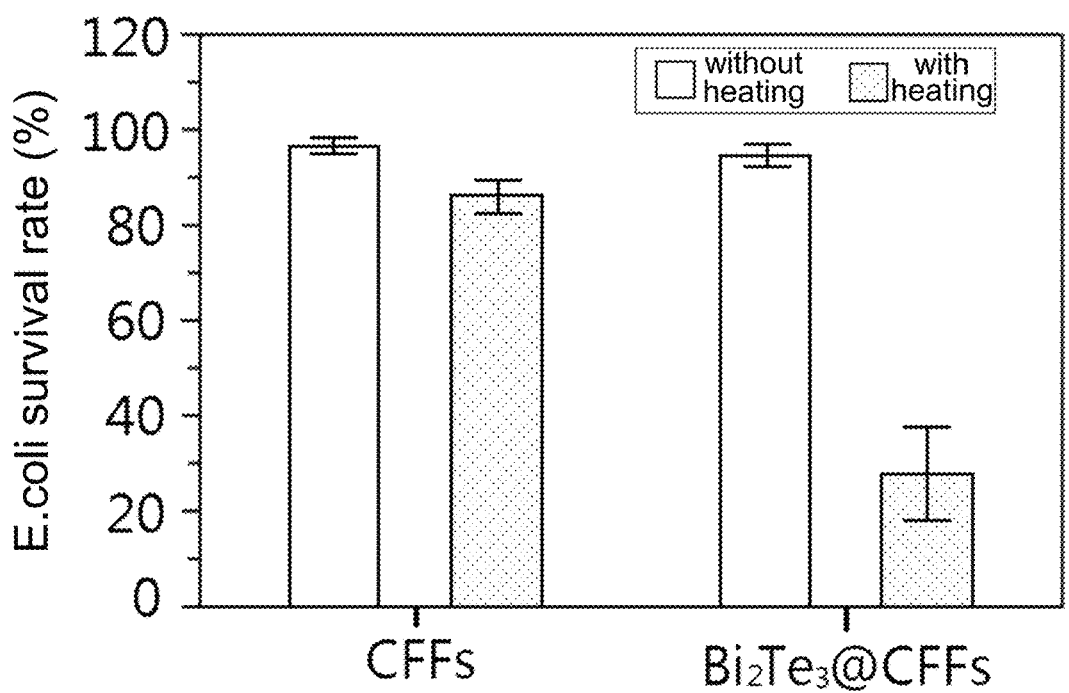
FIG. 6D is a bar graph of disinfection performance of the catalyst and a substrate of Experimental Example 4 under the temperature difference of FIG. 6B.

FIG. 6C is a bar graph of disinfection performance of the catalyst ($Bi_2Te_3$@CFF) and the substrate (CFF) under the temperature difference of FIG. 6A, and FIG. 6D is a bar graph of disinfection performance of the catalyst ($Bi_2Te_3$@CFF) and the substrate (CFF) under the temperature difference of FIG. 6B. From FIG. 6C and FIG. 6D, it can be observed that the CFF without $Bi_2Te_3$ exhibits a poor sterilization effect with regardless heating or cooling, while the catalyst of the disclosure has an obvious sterilization effect regardless of whether the temperature difference is positive or negative.

In order to verify the reusability of the catalyst of the disclosure, the following test was performed.

<Experimental Example 5> Reusability Test

Figure 7A:
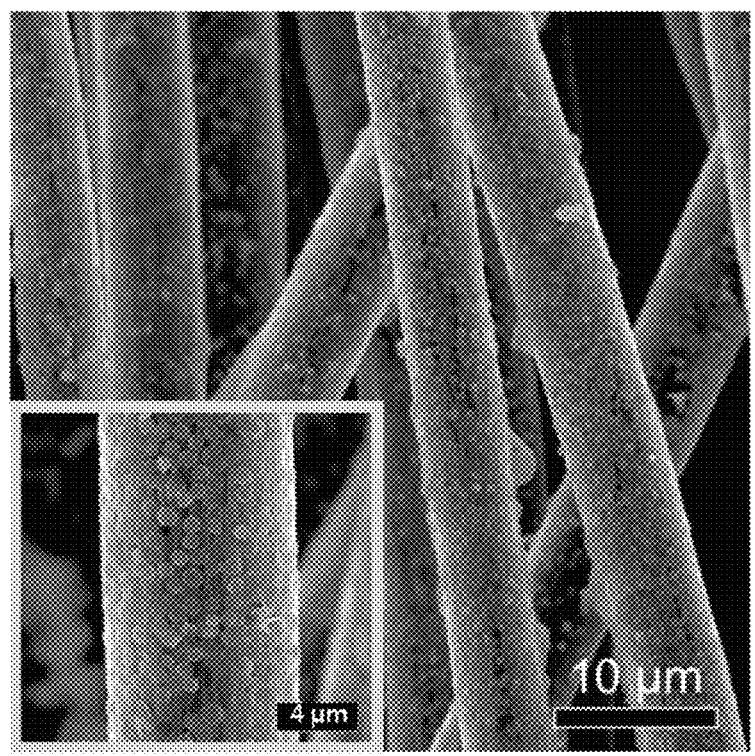
FIG. 7A is an SEM image of a catalyst of Experimental Example 5.

First, $Bi_2Te_3$@CFF with dimensions of 8×15 cm was prepared based on Preparation Example 2 and observed with an FESEM, and an image of FIG. 7A was obtained. From FIG. 7A, it is evident that the $Bi_2Te_3$ nanoplate was uniformly deposited on the CFF.

Then, the $Bi_2Te_3$@CFF was mounted on an indoor unit of a split air conditioner. The temperature of the air conditioner was set to 17° C. (different from the 25° C. room temperature by 8° C.), where the temperature difference is similar to that generated by the use of cooling fan in Experimental Example 4.

A disinfection (antibacterial) experiment was performed by using the same bacterial concentration ($2\times10^6$ CFU/mL) and environment (air) as in Experimental Example 4 and was repeated for 30 days. In addition, the survival rates of the bacteria were detected on different days. The results are shown in FIG. 7C.

Figure 7B:
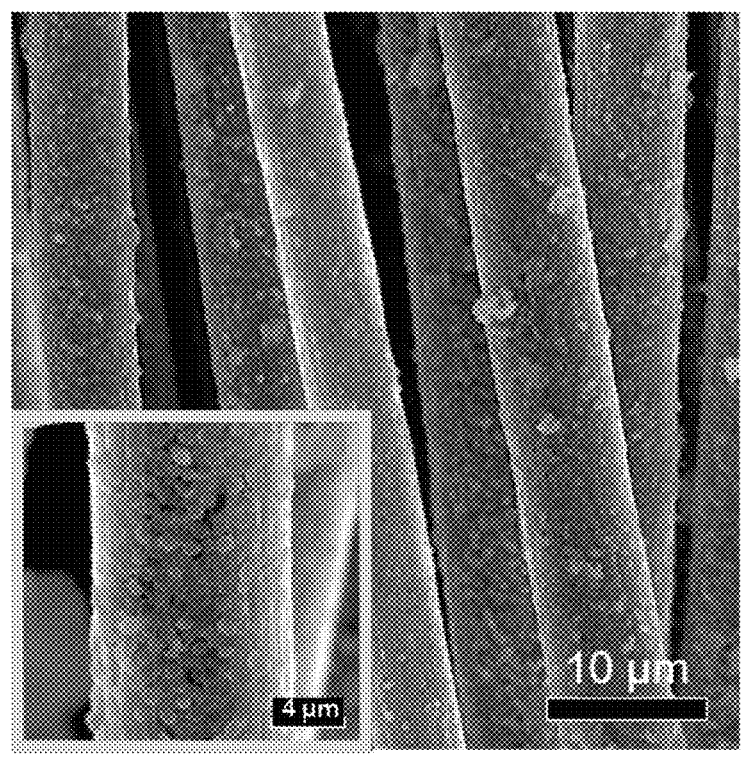
FIG. 7B is an SEM image of the catalyst of Experimental Example 5 after 30 days of use.

FIG. 7B is an SEM image of $Bi_2Te_3$@CFF after 30 days of use, with nearly no difference compared with FIG. 7A. Moreover, with XRD and Raman spectroscopy tests, the results show that after 30 days of test, the initial spectral property of $Bi_2Te_3$@CFF is still maintained as before the test.

Figure 7C:
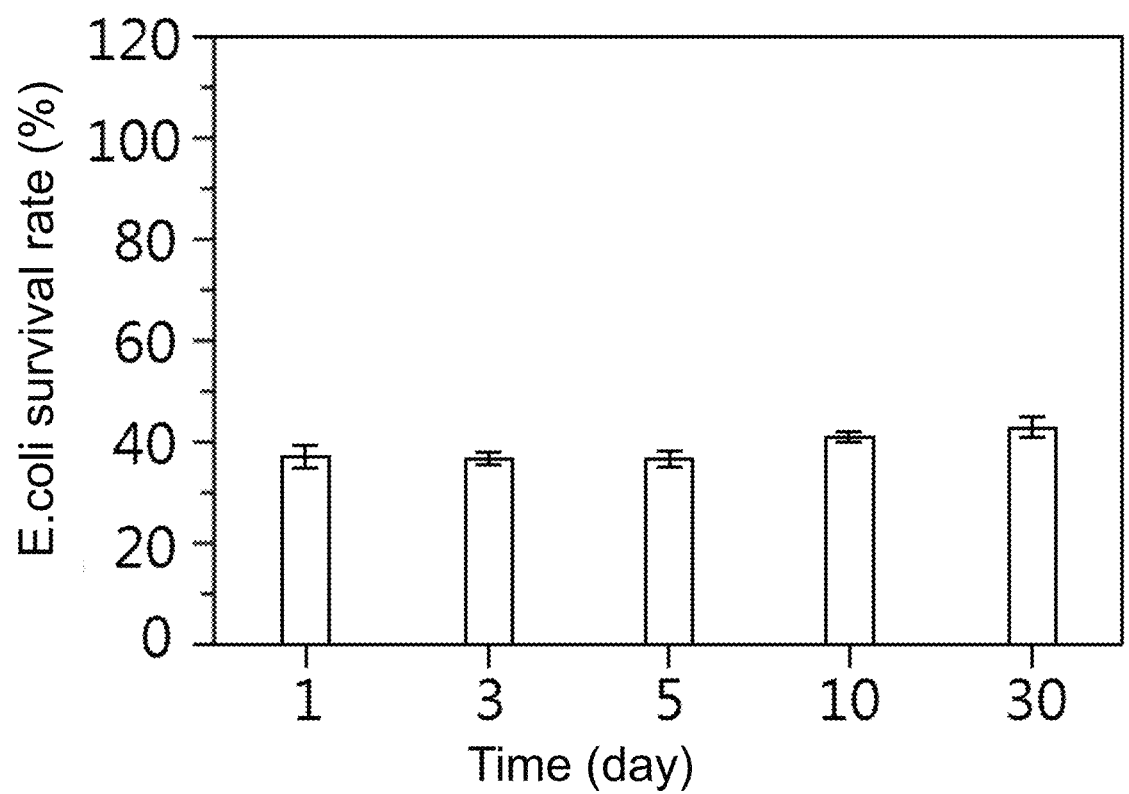
FIG. 7C is a bar graph of disinfection performance of the catalyst of Experimental Example 5 during the 30 days of use.

From FIG. 7C, it can be found that $Bi_2Te_3$@CFF exhibits similar disinfection performance and about 60% bacterial degradation across the 30 days of use, same as the results of Experimental Example 4 shown in FIG. 6C. Therefore, through this experiment, it can be verified that the long-term stability and robustness of the disclosure for practical disinfection applications.

In summary of the foregoing, the catalyst of the disclosure may serve to realize a low-cost antibacterial device that requires no external power source during its operation, and can be widely used in various daily necessities and equipment with good potential for development.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A catalyst for generating hydrogen peroxide induced by a temperature difference, the catalyst comprising:
   a plurality of thermoelectric materials, being distributed on a substrate and inducing a reaction between water vapor and oxygen contained in air through a temperature difference to generate hydrogen peroxide ($H_2O_2$) to serve a sterilization function through the hydrogen peroxide generated,
   wherein in a top view, the plurality of thermoelectric materials are independently dispersed on the substrate.

2. The catalyst as described in claim 1, wherein a form of the thermoelectric material comprises a nanomaterial or a bulk.

3. The catalyst as described in claim 2, wherein the nanomaterial comprises a nanoparticle, a nanoplate, or a nanowire.

4. The catalyst as described in claim 1, wherein the thermoelectric material is at least one material selected from a group consisting of a metal composite oxide, a polymer, a silicide, skutterudite, a Half-Heusler alloy, and a compound containing tellurium (Te).

5. The catalyst as described in claim 4, wherein the thermoelectric material comprises bismuth telluride ($Bi_2Te_3$), antimony telluride ($Sb_2Te_3$), or lead telluride (PbTe).

6. The catalyst as described in claim 1, wherein the substrate comprises a sheet substrate, a porous substrate, or a mesh substrate.

7. The catalyst as described in claim 1, wherein a concentration of the hydrogen peroxide generated is modulated through a content of the thermoelectric material and/or a magnitude of the temperature difference.

8. The catalyst as described in claim 1, wherein the thermoelectric material is formed on the substrate by coating, spraying, or soaking.

9. A method for environmental disinfection comprising:
   providing a catalyst for generating hydrogen peroxide induced by a temperature difference, wherein the catalyst comprises:
   a plurality of thermoelectric materials being distributed on a substrate, wherein in a top view, the plurality of thermoelectric materials are independently dispersed on the substrate;
   placing the catalyst in an environment with the temperature difference; and
   causing the catalyst to induce a reaction between water vapor and oxygen contained in air through the temperature difference to generate the hydrogen peroxide without applying power, and serve a sterilization function through the hydrogen peroxide generated.

10. The method as described in claim 9, wherein the environment with the temperature difference comprises an air outlet of an air conditioner, a heater, a fan, or a stove.

11. The method as described in claim 9, wherein the environment with the temperature difference comprises a surface of a mask.

12. The method as described in claim 9, wherein the environment with the temperature difference comprises an exterior wall or a window of a building.

\* \* \* \* \*